United States Patent [19]

Breda et al.

[11] 4,419,198

[45] Dec. 6, 1983

[54] PURIFICATION OF METHIOINE HYDROXY ANALOGUE HYDROLYZATE BY ELECTRODIALYSIS

[75] Inventors: Ernest J. Breda, Beaumont, Tex.; Kenneth B. Keating, Wilmington, Del.

[73] Assignee: Monsanto Company, St. Louis, Mo.

[21] Appl. No.: 275,670

[22] Filed: Jun. 22, 1981

[51] Int. Cl.³ .............................................. B01D 13/02
[52] U.S. Cl. .............................................. 204/180 P
[58] Field of Search .................... 204/180 P, 151, 131

[56] References Cited

U.S. PATENT DOCUMENTS 3,788,959  1/1974  Smith ................................ 204/180 P
3,933,610  1/1976  Ehara et al. ..................... 204/180 P

*Primary Examiner*—John F. Niebling
*Attorney, Agent, or Firm*—George R. Beck

[57] ABSTRACT

A process for separating anions, such as sulfates, chlorides and phosphates, and cations, such as ammonium and hydrogen ion, from methionine hydroxy analogue hydrolysate in solution by passing a direct electric current through an electrodialysis cell, said process producing substantial environmental benefits and energy savings over existing methods of manufacture.

8 Claims, 2 Drawing Figures

PURIFICATION OF METHIOINE HYDROXY ANALOGUE HYDROLYZATE BY ELECTRODIALYSIS

This invention relates to a proceess of separating ions, particularly sulfates, from methionine hydroxy analogue hydrolysate.

The hydroxy analogue of methionine is a well known chemical compound which is otherwise described as α-hydroxy-γ-methylmercaptobutyric acid (hereinafter referred to as MHBA) and also called 2-hydroxy-4-(methylthio)butyric acid. This compound has nutrient value equivalent to the corresponding amino acid, methionine. The calcium salt of MHBA, calcium-2-hydroxy-4-(methylthio)butyrate, is also known, and it is in this form that it is used to fortify animal feeds.

MHBA is generally prepared by hydrolysis of 2-hydroxy-4-(methylthio)butyronitrile, also known as α-hydroxy-γ-methylmercaptobutyronitrile (hereinafter referred to as MHBN), with an inorganic acid such as sulfuric acid or hydrochloric acid (U.S. Pat. No. 2,745,745, Blake and Wineman) or phosphoric acid (Br No. 1,080,667, Chemical and Phosphate Ltd., Israel). Economic and technical considerations generally favor either sulfuric or hydrochloric acid hydrolysis. The hydrolysis with sulfuric acid illustrated in Equation (1):

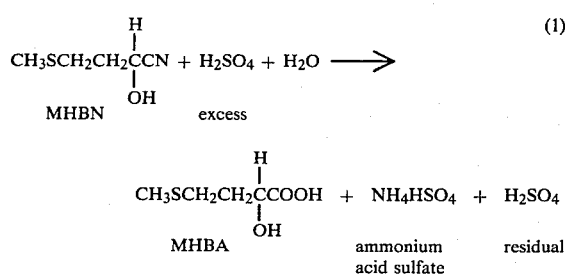

To prepare the calcium salt of MHBA, the MHBA hydrolysate prepared as in Equation (1) is neutralized by reaction with aqueous lime slurry (calcium hydroxide):

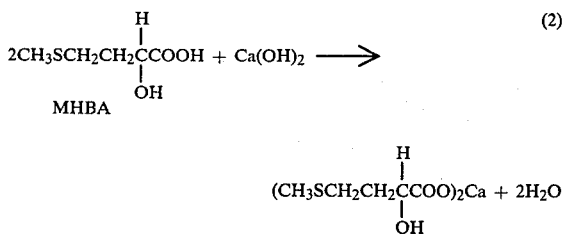

The product calcium salt is recovered from solution by evaporative crystallization, followed by washing and drying.

One of the by-products of the neutralization reaction illustrated in Equation (2) is calcium sulfate dihydrate, commonly known as gypsum. Gypsum is formed when the residual sulfuric acid and the ammonium acid sulfate present in the MHBA hydrolysate react with calcium hydroxide:

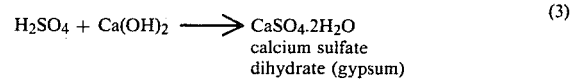

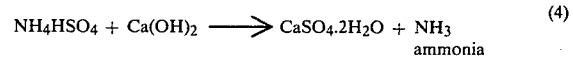

It has been found that as much as 1.6 pounds of gypsum may be formed for every pound of MHBA calcium salt formed in the neutralization reaction.

A number of undesirable side-effects are associated with the gypsum formation and handling. First, the gypsum must be disposed of in an environmentally safe fashion, a problem complicated by the fact that odoriferous impurities are often present in the gypsum waste. Second, since a portion of the lime used in the neutralization reaction is taken up in gypsum formation, more lime than the theoretical amount necessary to produce the product calcium salt must be used. This not only increases the cost of materials but also greatly increases energy costs. Extra water must be added to the system with the extra lime, and this water must eventually be removed in the energyintensive evaporative crystallization step. Finally, the gypsum tends to foul the equipment used in the manufacture of the calcium salt of MHBA, increasing maintenance costs and decreasing productive capacity due to downtime losses. There is therefore a clear need for a method of avoiding gypsum formation in the preparation of the calcium salt of MHBA. For similar reasons, it is desirable to avoid the formation of calcium chloride or calcium phosphate which can occur following hydrochloric or phosphoric acid hydrolysis of MHBN.

SUMMARY OF THE INVENTION

A new process has now been found whereby ions, particularly sulfates, chlorides, and phosphates, and ammonia are removed from the reaction mixture of MHBA obtained by acid hydrolysis of MHBN. Following the removal of said ions from the reaction mixture, the MHBA can be neutralized by reaction with calcium hydroxide with little or no formation of gypsum and other undesirable by-products.

This new process comprises:
  (i) introducing the reaction mixture into an electrolytic cell, said cell having at least three compartments, an anode compartment containing anolyte and having an anode in contact with said anolyte, a cathode compartment containing catholyte and having a cathode in contact with said catholyte, separated by at least one process compartment into which said reaction mixture is introduced, an anion-exchange membrane separating said anode compartment from said process compartment, and a cation-exchange membrane separating said cathode compartment from said process compartment; said anolyte and said catholyte being selected from water of aqueous sulfuric acid containing up to about 10% sulfuric acid;
  (ii) applying a direct current of electricity through the cell such that up to about 450 Ampere-hours of electrical charge are passed per liter of reaction mixture, the current being driven by an applied voltage of about 2 to 20 volts per cell; and
  (iii) recovering the purified MHBA reaction mixture.

The electrolytic cell may have more than three compartments in which case the anode and cathode compartments are separated by alternating process and receiving compartments which are, in turn, separated by alternating anion and cation-exchange membranes. In the multi-compartment cell, the MHBA reaction mixture is introduced into the process compartments and an electrolyte is introduced into the anode, cathode and receiving compartments.

DETAILED DESCRIPTION OF THE INVENTION

Figure 1:
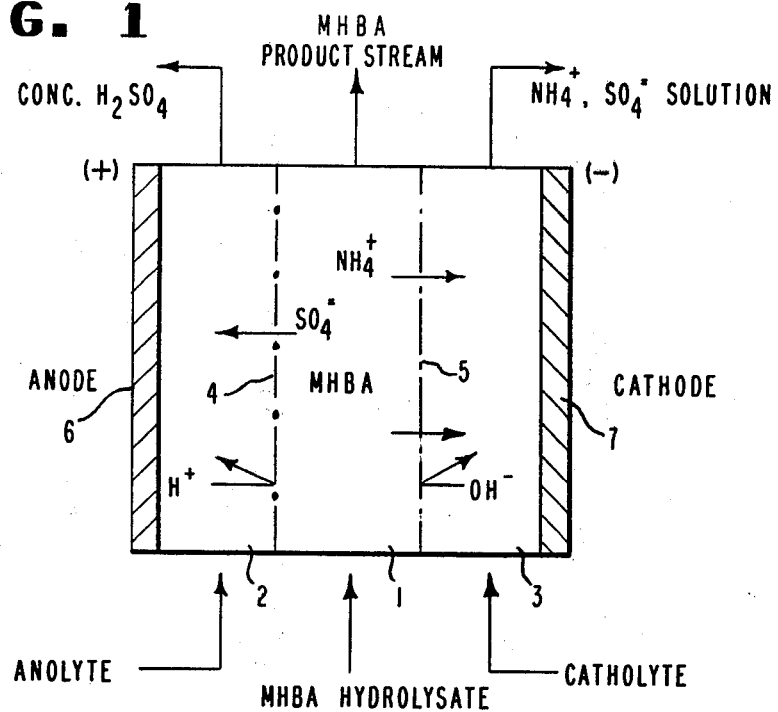

The process of this invention can be run as either a batch process or as a continuous process. One embodiment, a continuous process for removing sulfate and ammonium ions from a MHBA sulfuric acid hydrolysate, is described by reference to FIG. 1.

The MHBA hydrolysate, consisting essentially of MHBA, ammonium acid sulfate, sulfuric acid, and water, is introduced into the process compartment 1 of an electrolytic cell. The cell has three compartments, an anode compartment 2 receiving anolyte and discharging aqueous sulfuric acid and a cathode compartment 3 receiving catholyte and discharging aqueous ammonium sulfate, the anode and cathode compartments being separated by the process compartment.

Separating the process compartment from the anode and cathode compartments are, respectively, an anion-exchange membrane 4 and a cation-exchange membrane 5. Any number of commercially-available exchange membranes can be utilized, and one skilled in the art would be able to select an operable candidate. Membranes which have been used successfully in this work include Ionics Type 103-QZL-386 anion exchange membrane (Ionics, Inc., Watertown, MA) and Du Pont NAFION Type 324 perfluorinated membrane (E. I. du Pont de Nemours and Co., Inc., Wilmington, DE). Other membranes which could be used are among those listed in *Perry's Chemical Engineers' Handbook*, 1973, Sec. 17, page 53, the disclosure of which is herein incorporated by reference.

As with the ion-exchange membranes, the anode 6 and cathode 7 may be selected from a number of commercially available electrodes. The electrodes can be fabricated from any electrically conductive material which will not be readily consumed by the cell contents with which they come into contact. A platinum anode and a stainless steel cathode have proven to be suited to the process of this invention. At the platinum anode, water is oxidized, liberating oxygen gas and giving up electrons to the external circuit and releasing hydrogen ions to the anolyte; at the cathode, water is reduced, by reaction with electrons to hydrogen gas liberating hydroxyl ions to the catholyte.

Water or dilute aqueous sulfuric acid containing up to about 10% sulfuric acid, preferably about 0.4 to 0.6%, are suitable for use as anolyte and catholyte in this invention. When removing sulfate ions from the MHBA reaction mixture, it may be advantageous to maintain the sulfate concentration in the anode compartment at a lower level than that in the process compartment in order to maintain good coulombic efficiency for removal of sulfates. It is believed that this can be advantageous because the sulfate ions move to the anode compartment by diffusion as well as by electromigration. A low concentration of sulfate ions in the anolyte can be maintained by using a large volume of anolyte relative to hydrolysate (and recirculating it, if necessary), or by purging some of the sulfate ions which have been transferred to the anolyte, or both.

A direct current can be supplied to the cell by applying a voltage of 2 to 20 volt per cell such that up to about 450 Ampere-hours of electrical charge are passed per liter of reaction mixture. The required flow of current will vary, depending on the composition of the reaction mixture to be purified, and can be readily determined by one skilled in the art. The extent of ion migration will be proportional to the charge passed. Anions, e.g. $SO_4^=$ and $HSO_4^-$, migrate under the influence of the voltage gradient from the center compartment to the anode compartment, and cations, e.g. $NH_4^+$ and $H^+$, migrate to the cathode compartment. If chloride and/or phosphate anions are present, these too will migrate from the center compartment to the anode compartment. In the anode compartment sulfuric acid is formed by reaction of the migrated $SO_4^=$ and $HSO_4^-$ ions and the hydrogen ions released into solution at the anode. If desired, the concentration of the solution discharged from the anode compartment can be increased by the addition of 98% sulfuric acid and the resulting acid recycled to the hydrolysis reaction (Equation (1)). The cathode compartment, by virtue of the formation of hydroxyl ion as water is consumed, accumulates ammonium hydroxide as well as ammonium sulfate. The MHBA product stream in the center compartment, which can optionally be recycled through the electrolytic cell to insure substantial sulfate removal, can be neutralized with calcium hydroxide without formation of the gypsum by-product.

The process described above, using a three-compartment cell, results in three product streams, aqueous sulfuric acid from the anode compartment, aqueous ammonium sulfate from the cathode compartment and substantially purified MHBA from the process compartment. This process has the advantage that the aqueous sulfuric acid can be recycled as either anolyte in the continuous process or can be strengthened and recycled to the MHBN hydrolysis step.

Figure 2:
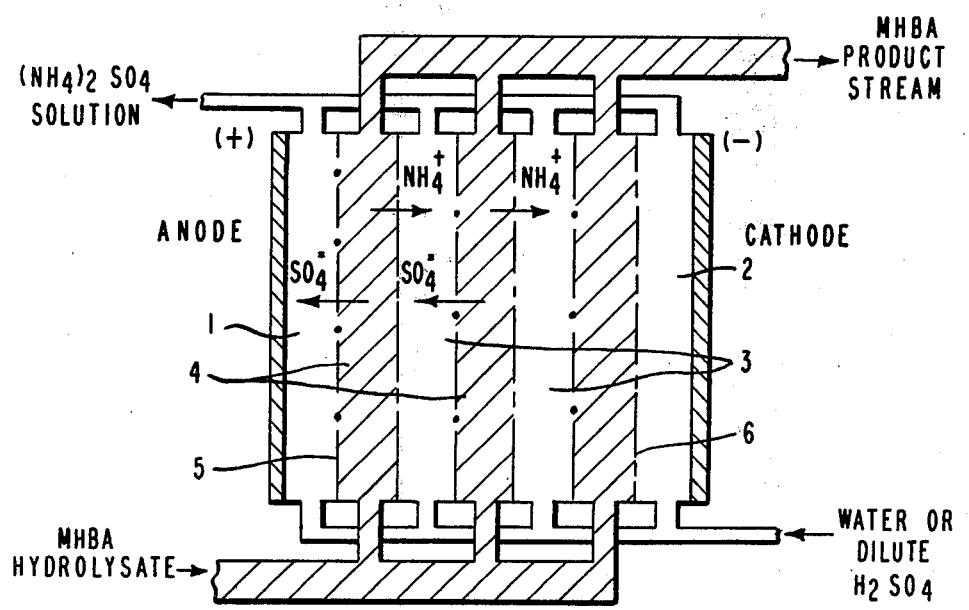

It is possible, however, to use a multi-compartment cell as illustrated in FIG. 2. In this cell, the anode compartment 1 and cathode compartment 2 are separated by alternating receiving compartments 3 and process compartments 4. All compartments are separated by alternating anion-exchange and cation exchange membranes 5 and 6, respectively. MHBA hydrolysate is continuously introduced into the process compartments and electrolyte (water or dilute $H_2SO_4$, as previously described) is introduced into the anode, cathode and receiving compartments. When a current is passed through the cell, sulfate and ammonium ions migrate into the receiving compartments to produce a dilute aqueous ammonium sulfate solution, leaving a purified MHBA solution. The optimal number of compartments utilized in a cell of this type can be determined by one skilled in the art.

This invention is further illustrated by the following example.

EXAMPLE

An experiment was performed in an electrodialysis cell fabricated from LUCITE, containing three compartments, each compartment having a chamber which was 1 inch deep and 3.5 inches in diameter. The compartments were separated by membranes as referred to in the section entitled Detailed Description of the Invention. The membranes were fixed in place by use of a General Electric RTV Silicone cement. The center compartment and the cathode compartment were outfitted with overflow tubes; the anode compartment was arranged so that anolyte could be pumped in and out of that compartment from a 10-gallon (37.5 liter) reservoir, thus keeping the concentration of sulfate, augmented by transfer into the anolyte from the hydrolysate, low with respect to the sulfate concentration in the hydrolysate. This is a useful, but not absolutely necessary, condition.

150 ml (202.5 g) of sulfuric acid (MHBA) hydrolysate was charged to the center compartment of the electrodialysis cell referred to above. The following is a summary of its physical particulars.

| Type Cell | Batch, 3-compartment |
|---|---|
| Capacity | 150 ml. solution each compartment |
| Cell Thickness | 2.54 cm each compartment |
| Cell Membrane Area (Each) | 62.1 cm$^2$ (0.067 sq. ft.) |
| Anode | Platinum |
| Cathode | 316 stainless steel |
| Anion Exchange Membrane | Ionics Type 103-QZL-386 |
| Cation Exchange Membrane | Du Pont NAFION Type 324 |

Anolyte was continuously recirculated into the anode compartment and back to the reservoir. Its initial concentration was 0.5% sulfuric acid (by weight).

Current was passed through the cell according to the following schedule:

3 Ampere for 10 minutes (0.5 Ampere-hour)
2.5 Amperes for 7 minutes (0.29 Ampere-hour)
2 Amperes for 5 minutes (0.17 Ampere-hour)
1.5 Amperes for 23 minutes (0.575 Ampere-hour)
1.0 Ampere for 21 hours 11 minutes (21.18 Ampere-hour)

The voltage on the cell during this experiment was between 15 and 20 volts.

This schedule resulted in a total of 22.72 Ampere-hours being applied to the cell. At the end of the experiment, the contents of the center compartment and the catholyte compartment were weighed and the anolyte, catholyte and center compartment were analyzed for ammonia, sulfate and methionine hydroxy analogue.

The results are tabulated in Table I. It can be readily shown that 62% of the sulfate has been removed from the center compartment, 42% of the ammonia has been removed and approximately 75% of the MHBA has been retained. The system can be readily optimized with respect to ion removal and MHAA retention by varying membranes, charge passed per unit volume, flow rates and other variables.

TABLE I

REMOVAL OF SULFATES AND AMMONIA
FROM PRECURSOR SULFURIC ACID HYDROLYSATE
DISTRIBUTION OF SPECIES

|  | Hydrolysate in center compartment at start of experiment | Final anolyte | Final center compartment | Final catholyte |
|---|---|---|---|---|
| Weight (g.) | 202.5 | — | 163.4 | 107.8 |
| % MHBA | 34.5 | trace | 31.87 | 1.93 |
| g MHBA | 69.86 | Unk. | 52.07 | 2.08 |
| % SO$_4^=$ | 35.94 | trace | 16.98 | 1.72 |
| g SO$_4^=$ | 72.78 | Unk. | 27.74 | 1.85 |
| % NH$_3$ | 3.91 | 0.0 | 2.82 | 1.42 |
| g NH$_3$ | 7.92 | 0.0 | 4.60 | 1.53 |

What is claimed is:

1. A process for separating anions and cations from a reaction mixture obtained by acid hydrolysis of MHBN to MHBA comprising:
   (i) introducing the reaction mixture into an electrolytic cell, said cell having at least three compartments, an anode compartment containing anolyte and having an anode in contact with said anolyte, a cathode compartment containing catholyte and having a cathode in contact with said catholyte, separated by at least one process compartment into which said reaction mixture is introduced, an anion-exchange membrane separating said anode compartment from said process compartment, and a cation-exchange membrane separating said cathode compartment from said process compartment; said anolyte and said catholyte being selected from water or aqueous sulfuric acid containing up to about 10% sulfuric acid;
   (ii) applying a direct current of electricity through the cell such that up to about 450 Ampere-hours of electrical charge are passed per liter of reaction mixture, the current being driven by an applied voltage of about 2 to 20 volts per cell; and
   (iii) recovering the purified MHBA reaction mixture.

2. The process of claim 1 where sulfate and ammonium ions are removed from a reaction mixture obtained by sulfuric acid hydrolysis of MHBN to MHBA.

3. The process of claim 2 where the concentration of sulfate ion in the process compartment or compartments exceeds that in the anode compartment.

4. The process of claims 1, 2 or 3 where the anolyte and catholyte are aqueous sulfuric acid containing about 0.4 to 0.6% sulfuric acid.

5. The process of claim 1 where the reaction mixture is introduced into a multi-compartment electrolytic cell in which the anode compartment and the cathode compartment are separated by a series of alternating process and receiving compartments, all compartments are separated from one another by alternating anion- and cation-exchange membranes, the reaction mixture being introduced into the process compartments, and an electrolyte selected from water or aqueous sulfuric acid containing up to about 10% sulfuric acid being introduced into the anode, cathode and receiving compartments.

6. The process of claim 5 where sulfate and ammonium ions are removed from a reaction mixture obtained by sulfuric acid hydrolysis of MHBN to MHBA.

7. The process of claim 6 where the concentration of sulfate ion in the process compartments exceeds that in the anode and receiving compartments.

8. The process of claims 5, 6 or 7 where the electrolyte is aqueous sulfuric acid containing about 0.4 to 0.6% sulfuric acid.

* * * * *